US009016111B2

(12) United States Patent
Stukan et al.

(10) Patent No.: US 9,016,111 B2
(45) Date of Patent: Apr. 28, 2015

(54) METHODS FOR DETERMINING WETTABILITY ALTERATION

(71) Applicant: Schlumberger Technology Corporation, Sugar Land, TX (US)

(72) Inventors: Mikhail Stukan, Al-Khobar (SA); Wael Abdallah, Al-Khobar (SA)

(73) Assignee: Schlumberger Technology Corporation, Sugar Land, TX (US)

( * ) Notice: Subject to any disclaimer, the term of this patent is extended or adjusted under 35 U.S.C. 154(b) by 402 days.

(21) Appl. No.: 13/693,944

(22) Filed: Dec. 4, 2012

(65) Prior Publication Data
US 2013/0152668 A1 Jun. 20, 2013

Related U.S. Application Data

(60) Provisional application No. 61/570,589, filed on Dec. 14, 2011.

(51) Int. Cl.
*G01N 13/00* (2006.01)
*G01N 13/02* (2006.01)

(52) U.S. Cl.
CPC ........ G01N 13/02 (2013.01); *G01N 2013/0208* (2013.01)

(58) Field of Classification Search
CPC ............... G01N 13/02; G01N 2013/0208
USPC ........................................... 73/64.48
See application file for complete search history.

(56) References Cited

U.S. PATENT DOCUMENTS

| 6,121,048 | A * | 9/2000 | Zaffaroni et al. ........... 506/14 |
| 2009/0078326 | A1 * | 3/2009 | Rosario et al. ............ 137/827 |
| 2010/0126702 | A1 * | 5/2010 | Tsunemori et al. ...... 165/104.29 |

OTHER PUBLICATIONS

Abdallah, et al., "Fundamentals of Wettability", Oilfield Review, vol. 19(2), May 2007, pp. 44-61.
Anderson, William, "Wettability Literature Survey—Part 2: Wettability Measurement", Journal of Petroleum Technology, vol. 38(11), Nov. 1986, pp. 1246-1262.
Bartell, et al., "Determination of the Wettability of a Solid by a Liquid", Industrial & Engineering Chemistry, vol. 19(11), 1927, pp. 1277-1280.
Goossens, et al., "Can We Predict the Spreading of a Two-Liquid System from the Spreading of the Corresponding Liquid-Air Systems?", Langmuir, vol. 27 (16), 2011, pp. 9866-9872.
Ligthelm, et al., "Novel Waterflooding Strategy by Manipulation of Injection Brine Composition", SPE 119835—EUROPEC/EAGE Conference and Exhibition, Amsterdam, The Netherlands, Jun. 8-11, 2009, 22 pages.

(Continued)

*Primary Examiner* — Hezron E Williams
*Assistant Examiner* — Rodney T Frank
(74) *Attorney, Agent, or Firm* — Bridget Laffey; Jakub Michna; Daniel Matthews

(57) ABSTRACT

A protocol for determining the effect of water composition on surface alteration is described using simple and less preparation sensitive, brine/oil and rock/brine/air systems when compared to conventional rock/brine/oil measurement methods. A model glass/brine/oil system is described and it is demonstrated that experimental measurements of contact angle obtained using a conventional approach agree well with the contact angles predicted using the proposed protocol.

30 Claims, 7 Drawing Sheets

(56) References Cited

OTHER PUBLICATIONS

Okasha, et al., "Effect of Brine Salinity on Interfacial Tension in Arab-D Carbonate Reservoir, Saudi Arabia", SPE 119600—SPE Middle East Oil and Gas Show and Conference, Bahrain, Bahrain, May 15-18, 2009, 9 pages.

Seethepalli, et al., "Wettability Alteration During Surfactant Flooding of Carbonate Reservoirs", SPE 89423—SPE/DOE Symposium on Improved Oil Recovery, Tulsa, Oklahoma, Apr. 17-21, 2004, 10 pages.

Stukan, et al., "Interfacial Tension (IFT) and Surface Alteration Interplay", SPE 161279-PP—SPE International Petroleum Exhibition & Conference, Abu Dhabi, Nov. 11-14, 2012, pp. 1-10.

Swenson, et al., "A Novel Centrifugal Method for Wettability Characterization of Granulates", Industrial & Engineering Chemistry Research, vol. 50(9), 2011, pp. 5565-5574.

Yousef, et al., "New Recovery Method for Carbonate Reservoirs through Tuning the Injection Water Salinity: Smart WaterFlooding", SPE 143550—SPE EUROPEC/EAGE Annual Conference and Exhibition, Vienna, Austria, May 23-26, 2011, 16 pages.

* cited by examiner

METHODS FOR DETERMINING WETTABILITY ALTERATION

CROSS REFERENCE TO RELATED APPLICATIONS

This application claims benefit of U.S. Provisional Patent Application Ser. No. 61/570,589 filed Dec. 14, 2011, which is incorporated herein by reference in its entirety.

FIELD

The subject disclosure generally relates to methods for determining wettability alteration due to fluid changes. In particular, the subject disclosure relates to methods for determining contact angle alteration in rock/brine/oil systems due to changes in brine compositions.

BACKGROUND

In the oilfield industry, two main parameters are used to assess enhanced oil recovery (EOR) techniques in terms of its efficiency: interfacial tension and surface (wettability) alteration. The impact of these parameters on recovering what is left in the reservoir is important. Although, there is currently an interest in brine injection as a potential-EOR method, the role of interfacial tension and wettability alteration is not well understood. In a hydrocarbon reservoir, when brine and oil come in contact, they create a particular angle with the rock surface. If the brine concentration changes, such as being reduced by pumping fresh water or seawater into the reservoir, the corresponding contact angle changes.

Conventional techniques of contact angle measurements on reservoir rocks at downhole conditions are very complicated. They are highly sensitive and require good core preservation and preparation. Accordingly, there is a need for better understanding of the role of interfacial tensions and wettability, as well as improved methods for determining wettability alteration due to changes in fluid composition.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

According to some embodiments, a method is described for determining wettability alteration due to fluid changes. The method includes: measuring interfacial tensions between a first liquid and a second fluid, and between the first liquid and a third fluid; measuring surface tensions between the second and third fluid and a first reference fluid; measuring contact angle of the first liquid and a first solid surface in a second reference fluid; measuring contact angles of the second and third fluids and the first solid surface in the first reference fluid; and determining a change in wettability for the first solid surface and the first liquid due to a change from the second fluid to the third fluid based at least in part on the measurements of interfacial tensions, surface tensions and contact angles. According to some embodiments, the measurements are carried out at the same temperature and pressure. According to some embodiments the first reference fluid is air, and the second reference fluid is deionized water.

According to some embodiments, the steps of measuring the contact angles are repeated for a second and third solid surfaces, and the change in wettability for the second and third solid surfaces and the first liquid due to a change from the second fluid to the third fluid is calculated based on the measurements of interfacial tensions, surface tensions, as well as on the measurements of contact angles with the second solid surface. According to some embodiments, the measurements of interfacial tension, surface tension and contact angle are repeated for a fourth and fifth fluid.

According to some embodiments, the change in wettability includes a calculation of a change in contact angle between the first liquid and the first solid surface due to a change from the second fluid to the third fluid. The calculated change in contact angle can be based on a relationship between change in contact angle, an interfacial tension term and a surface alteration term, where the interfacial tension term relates to a change in interfacial tension from between the first liquid and the second fluid to between the first liquid and the third fluid, and the surface alteration term relating to a change in interfacial tension from between the second fluid and the first surface to between the third fluid and the first surface.

According to some embodiments the first surface is a surface on a sample of rock, such as core sample, from a subterranean hydrocarbon-bearing reservoir rock formation, the first liquid is oil, and the second and third fluids are aqueous liquids such as brines having different compositions.

According to some embodiments, a system is described for determining wettability alteration due to fluid changes. The system includes a computer configured and programmed to receive data representing measurements of (1) interfacial tension between a first liquid and a second fluid, (2) interfacial tension between the first liquid and a third fluid, (3) surface tension between the second fluid and a first reference fluid, (4) surface tension between the third fluid and the first reference fluid, (5) contact angle of the first liquid and a first solid surface in a second reference fluid, (6) contact angle of the second fluid and the first solid surface in the first reference fluid, and (7) contact angle of the third fluid and the first solid surface in the first reference fluid, and to determine a change in wettability for the first solid surface and the first liquid due to a change from the second fluid to the third fluid based at least in part on the data representing the measurements of interfacial tensions, surface tensions and contact angles. According to some embodiments, the system further includes a borehole deployable core sampling tool adapted and configured to obtain a core sample from a subterranean hydrocarbon-bearing reservoir rock formation, and the first solid surface is a surface on a sample of rock from a core sample taken from the subterranean rock formation, the first liquid is an oil, the second and third fluids are aqueous liquids, and the second and third fluids are brines having different compositions.

BRIEF DESCRIPTION OF THE DRAWINGS

The subject disclosure is further described in the detailed description which follows, in reference to the noted plurality of drawings by way of non-limiting examples of embodiments of the subject disclosure, in which like reference numerals represent similar parts throughout the several views of the drawings, and wherein:

FIGS. 2-1 and 2-2 show drops of brine of different salinity at a surface in air, according to some embodiments;

FIGS. 5-1 and 5-2 are flow charts illustrating a protocol for determining contact angle changes, according to some embodiments.

DETAILED DESCRIPTION

Figure 1:
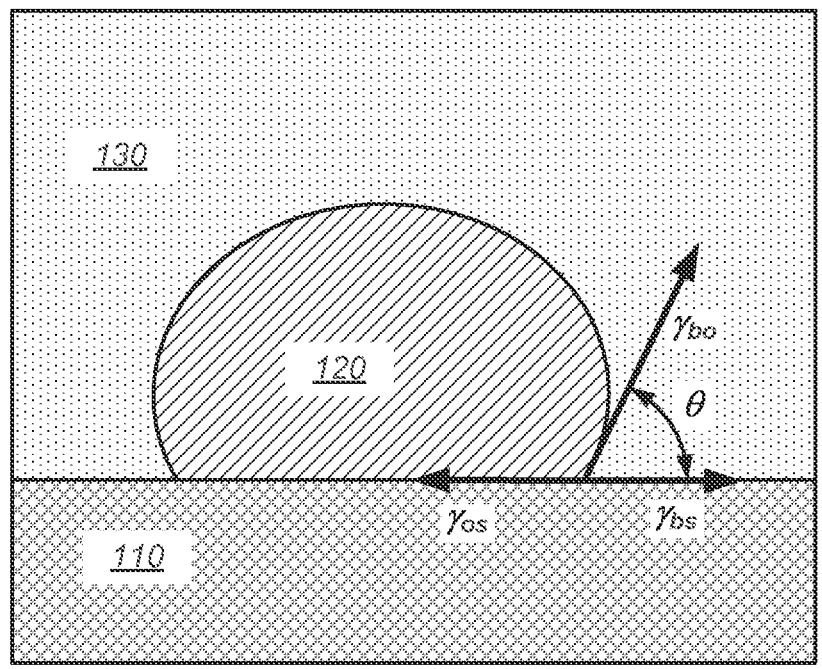
FIGS. 1-1 and 1-2 are diagrams illustrating a drop of oil on a surface in two brines having different salinity, according to some embodiments.

The particulars shown herein are by way of example and for purposes of illustrative discussion of the embodiments of the subject disclosure only, and are presented in the cause of providing what is believed to be the most useful and readily understood description of the principles and conceptual aspects of the subject disclosure. In this regard, no attempt is made to show structural details in more detail than is necessary for the fundamental understanding of the subject disclosure, the description taken with the drawings making apparent to those skilled in the art how the several forms of the subject disclosure may be embodied in practice. Furthermore, like reference numbers and designations in the various drawings indicate like elements.

Two main parameters for assessing an enhanced oil recovery (EOR) technique in terms of its efficiency are interfacial tension (IFT) and surface (wettability) alteration. The impact of these parameters on recovering what is left in the reservoir is often of great importance. With the current interest in brine injection as a potential-EOR method, it is of interest to better understand the role of IFT and wettability alteration in such process. According to some embodiments, a theoretical model is described to evaluate the impact of both parameters. The results of the described model indicate that in the case of carbonates, salinity injection has a greater effect on surface wettability than interfacial tension.

Conventional techniques of contact angle measurements on reservoir rocks at downhole conditions can be relatively complicated and inaccurate. The techniques are highly sensitive and depend greatly on good core preservation and preparation. According to some embodiments, a protocol is described to measure contact angle dependence on brine salinity, which includes a single contact measurement in a rock/brine/oil system using fresh water and a set of less complicated measurements in brine/oil and rock/brine/air systems. The results of the described predictive protocol for contact angle measurements have been found to be in very good agreement with conventional experimental measurements using a glass/brine/dodecane system. Using simple contact angle measurements on the surface in air to calculate contact angles at different salinities makes the utilization of the described protocol attractive and less sensitive to surface preparation and its complexity.

In a hydrocarbon reservoir, when brine and oil come in contact, they create a particular angle with the rock surface. If the brine concentration changes, such as being reduced by pumping fresh water or seawater into the reservoir, the corresponding contact angle changes. There are two background mechanisms for such a change. The first one is the change in brine/oil interfacial tension ($\gamma_{bo}$), which has been demonstrated by oil/brine measurements at reservoir conditions, and the second impact comes from the change of brine/rock surface wettability ($\gamma_{bs}$). The latter is related to, so called "surface alteration", which has also been demonstrated on core plugs. In order to understand which mechanism has a more drastic effect on the recovery, we describe a theoretical model combined with a few simple laboratory measurements to predict the impact of each of these two mechanisms.

In general, contact angle measurements on reservoir rocks by themselves are not the best approach to determine rocks wettability. Many different methods have been proposed for measuring the wettability of rock surface that include reservoir core samples in either native or restored states. Such measurements are either quantitative methods such as contact angles, Amott and USBM techniques, or qualitative methods, such as imbibition rates, microscope examination, flotation, glass slide method, relative permeability curves, permeability saturation relationships, capillary pressure curves, displacement capillary pressure, reservoir logs, nuclear magnetic resonance, and dye adsorption.

Although none of the above-mentioned techniques are widely accepted, contact angle, Amott and USBM techniques are currently the most frequently used in the industry. The contact angle approach provides the wettability of a specific surface, while the Amott and USBM methods provide the average wettability of a core. Unfortunately, these methods often lead to inconsistent results. Many of the wettability measurements are imprecise, time consuming, inaccurate, suffer from contamination and surface preparation issues and do not perform well at a neutral wettability range.

According to some embodiments, we describe a novel protocol of determining the effect of water composition on surface alteration using much simpler and less preparation sensitive, brine/oil and rock/brine/air systems instead of the complicated rock/brine/oil measurements. A model glass/brine/oil system is described, and it is demonstrated that experimental measurements of contact angle obtained using a conventional approach agree well with the contact angles predicted using the proposed protocol.

Experimental Setup and Measurements.

A First Ten Angstrom (FTA) sealed cell was used to measure pendant drop interfacial tension and contact angle for the studied systems. The cell capacity was 22 cc with a 25 mm view port window to allow light passage. The cell was mounted on an adjustable jacket in front of an optical system from KRÜSS (DSA100) and the overall setup was positioned on top of a vibration-free table for accurate measurements of IFT and contact angle. The IFT cell was sealed with viton o-rings and rated to 100 psi and 100° C. by circulating a heated fluid through two internal loops within the cell. A liquid drop for IFT measurements was formed using a stainless steel needle with tip diameter of 0.71 mm, while a needle of 0.41 mm was used for contact angle drops. A desktop computer was used to acquire the digital image of the pendant oil or brine drop and perform the subsequent drop image analysis, digitization, and computation. A DSA1 v1.9 drop shape analyzer from KRÜSS was used. The interfacial tension was calculated using the Young-Laplace equation.

The IFT cell body and its various parts were cleaned using acetone followed by deionized water when model alkanes and brines were used, then fully dried by air. Dodecane (reagent plus>99% purity) from Sigma-Aldrich® and deionized water purified by Millipore® system to <30 ppb TDS were used in our study. Microscope slides from Marienfeld Laboratory Glassware were used as the surface for contact angle measurements.

Theory.

Figures 1, 2:
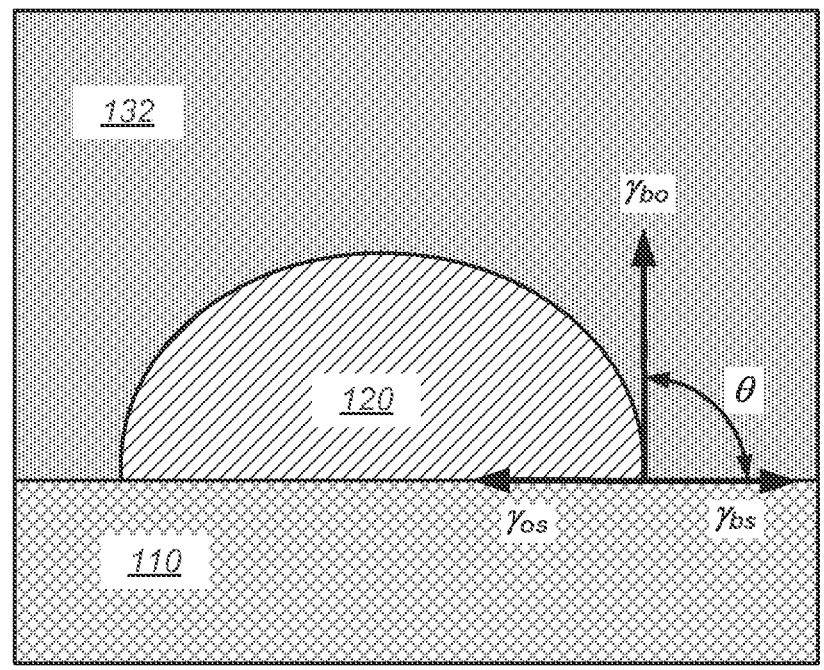
Figures 1, 2:
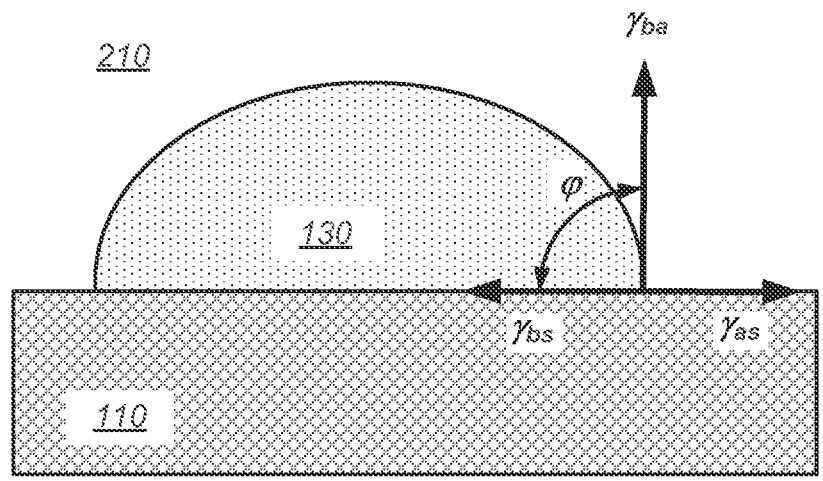
Figure 2:
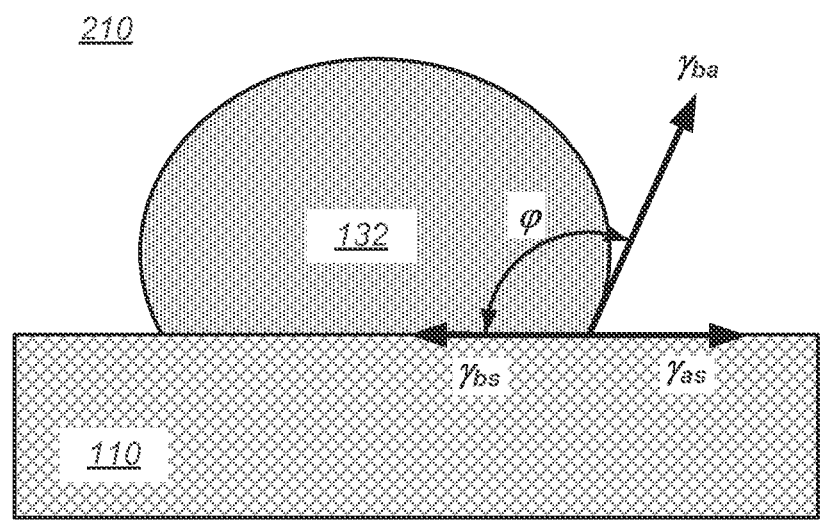

FIGS. 1-1 and 1-2 are diagrams illustrating a drop of oil on a surface in two brines having different salinity, according to some embodiments. The oil drop 120 is shown in each case on the surface of a solid material 110. In the case of FIG. 1-1, the surrounding fluid is brine 130 having a low salinity, while in FIG. 1-2, the surrounding fluid is brine 132 having a higher salinity. The equilibrium contact angle θ in solid/brine/oil system is determined by the Young-Laplace equation (Eq. 1):

$$\cos\theta = \frac{\gamma_{os} - \gamma_{bs}}{\gamma_{bo}} \quad (1)$$

where $\gamma_{bo}$ is brine/oil interfacial tension, $\gamma_{bs}$ is solid/brine surface tension and $\gamma_{os}$ is solid/oil surface tension. If we consider the system at two brine concentrations, namely a low concentration ($c_l$) as shown in FIG. 1-1, and a high concentration ($c_h$) as shown in FIG. 1-2, the difference in brine salinity will affect the contact angle in a way illustrated in FIGS. 1-1 and 1-2. Taking into account Eq. 1, and the fact that $\gamma_{os}$ does not depend on the brine concentration this difference in contact angle can be written as:

$$\cos\theta(c_l) - \cos\theta(c_h) = \frac{\gamma_{os} - \gamma_{bs}(c_l)}{\gamma_{bo}(c_l)} - \frac{\gamma_{os} - \gamma_{bs}(c_h)}{\gamma_{bo}(c_h)} \quad (2)$$

$$\Delta\cos\theta = \frac{|\gamma_{bs}(c_l) - \gamma_{os}|\Delta\gamma_{bo} - \gamma_{bo}(c_l)\Delta\gamma_{bs}}{\gamma_{bo}(c_l)\gamma_{bo}(c_h)} \quad (3)$$

Here, we introduced the following notations:

$$\Delta\cos\theta \equiv \cos\theta(c_l) - \cos\theta(c_h);$$

$$\Delta\gamma_{bo} \equiv \gamma_{bo}(c_l) - \gamma_{bo}(c_h); \text{ and}$$

$$\Delta\gamma_{bs} \equiv \gamma_{bs}(c_l) - \gamma_{bs}(c_h).$$

Note, when defined like that, Δ cos θ is positive (i.e. Δ cos θ>0) based on the experimental observations, we can rewrite Eq. 3 as:

$$\Delta\cos\theta = -\frac{\cos\theta(c_l)}{\gamma_{bo(c_h)}}\Delta\gamma_{bo} - \frac{1}{\gamma_{bo(c_h)}}\Delta\gamma_{bs} \quad (4)$$

where $$\gamma_{bs}(c_l) - \gamma_{os} = -\gamma_{bo}(c_l)\cos\theta(c_l)$$

In Eq. 4, we have two terms. The first one is related to the change in brine/oil IFT ($\Delta\gamma_{bo}$), while the second term describes the role of "surface alteration" ($\Delta\gamma_{bs}$). Since we are talking about differences between values of parameters at different states, it is useful to define a reference system. Although, in the reservoir one normally starts from the high salinity and then reduces it, for methodical and calculation reasons, according to some embodiments, it is preferable to choose as the reference state system with a brine salinity of c=0.0 (i.e. deionized water). This approach is used through many of the embodiments described herein.

Results and Discussion—Surface Alteration vs. Interfacial Tension.

Let us start with the second ("surface alteration") term. While the value of brine/oil IFT $\gamma_{bo}$ is known or/and is a reasonably easy measurable parameter, it is not the case for surface/brine interfacial tension ($\gamma_{bs}$). Fortunately, we do not need values of $\gamma_{bs}(c_l)$ and $\gamma_{bs}(c_h)$ themselves, but rather we can use the difference ($\Delta\gamma_{bs} = \gamma_{bs}(c_l) - \gamma_{bs}(c_h)$). To calculate $\Delta\gamma_{bs}$, we can consider drops of brine of salinities $c_l$ and $c_h$ at the same surface in the air. FIGS. 2-1 and 2-2 show drops of brine of different salinity at a surface in air, according to some embodiments. In FIG. 2-1, a drop of low salinity brine 130 is shown on the surface of the solid material 110 and in FIG. 2-2 a drop of high salinity brine 132 is shown on the surface 110. In both cases the drops of brine 130 and 132 are surrounded by air 210. Using again Young-Laplace equation (Eq. 1), we can write (since air/solid IFT $\gamma_{as}$ does not depend on brine salinity):

$$\gamma_{bs}(c_l) + \gamma_{ba}(c_l)\cos\phi(c_l) = \gamma_{bs}(c_h) + \gamma_{ba}(c_h)\cos\phi(c_h)$$

Thus:

$$\Delta\gamma_{bs} = \gamma_{ba}(c_h)\cos\phi(c_h) - \gamma_{ba}(c_l)\cos\phi(c_l) \quad (5)$$

Contact angles (φ) for a surface/brine/air system such as shown in FIGS. 2-1 and 2-2, and surface tension values for brine/air ($\gamma_{ba}$), can be measured experimentally. Such measurements were performed for brines (NaCl) of four different salinities using sessile drop and pendant drop systems. The experimental values of the contact angle in a calcite/brine/air system after 3-minute relaxation $\phi_3$, and well equilibrated (1 hours), $\phi_{1h}$, are provided in Table 1. In Table 1, the values of contact angle φ for drops of brine at a calcite surface in the air and the difference in surface/brine surface tension $\Delta\gamma_{bs}$ for each different concentration of the brine. As the reference state system with DI water (c=0.0) is chosen.

TABLE 1

| c, (mol/kg) | c, kppm | $\phi_3$, deg | $\phi_{1h}$, deg | $\Delta_3\gamma_{bs}$, mN/m | $\Delta_{1h}\gamma_{bs}$, mN/m |
|---|---|---|---|---|---|
| 0.00 | 0.00 | 98 | 90.7 | 0.00 | 0.00 |
| 1.91 | 100.4 | 105 | 103.2 | −9.54 | −16.39 |
| 2.75 | 138.5 | 113 | 104.9 | −20.12 | −18.96 |
| 3.64 | 175.4 | 117 | 111.9 | −25.74 | −28.51 |

We measured dependence of $\gamma_{ba}$ on brine salinity using pendant drop technique (see Table 2 and FIG. 3) and obtained $\gamma_{ba} = 1.8335c + 72.135$ (here c is the brine concentration in molality (mol/kg), and γ is surface tension in mN/m). Using Eq. 5, we can calculate $\Delta\gamma_{bs}$ for different brine concentrations (see Table 1). As the reference state system with DI water (c=0.0) is chosen. Value of $\Delta\gamma_{bs}$ is always negative, which means that the second term in Eq. 4 always gives a positive contribution to Δ cos θ.

Consider now the first term in Eq. 4. Pendant drop experimental measurements for brine/oil interfacial tension provided:

$$\gamma_{bo} = 1.4505c + 52.5697 \quad (6)$$

for initial IFT value and:

$$\gamma_{bo} = 1.697c + 35.187 \quad (7)$$

for the IFT value after 10 hour equilibration.

Table 2 shows surface tension (brine/air), $\gamma_{ba}$, and interfacial tension (brine/dodecane), $\gamma_{bo}$, for brines of different salinity. Since $\gamma_{bo}$ exhibits strong time dependence, two sets of values (initial, and after 10 hours relaxation) are provided. *The values are obtained based on Eqs. 6 and 7 due to absence of experimental data.

TABLE 2

| | | | $\gamma_{bo}$, mN/m | |
|---|---|---|---|---|
| c, (mol/kg) | c, kppm | $\gamma_{ba}$, mN/m | 0 hrs | 10 hrs |
| 0.00 | 0.0 | 72.49 | 52.46 | 34.78 |
| 0.73 | 40.9 | 73.33 | 53.93 | 36.25 |
| 1.51 | 81.1 | 75.06 | 54.85 | 37.50 |
| 1.91 | 100.4 | 75.56 | 55.34* | 38.43* |
| 2.33 | 119.9 | 76.34 | 55.72 | 40.81 |
| 2.75 | 138.5 | 77.15 | 56.56* | 39.85* |
| 3.64 | 175.4 | 78.04 | 57.81 | 41.15 |

TABLE 2-continued

|  |  |  | $\gamma_{bo}$, mN/m | |
|---|---|---|---|---|
| c, (mol/kg) | c, kppm | $\gamma_{ba}$, mN/m | 0 hrs | 10 hrs |
| 4.10 | 193.3 | 79.73 | 58.52* | 42.14* |
| 4.57 | 210.8 | 80.37 | 58.80 | 42.07 |
| 5.06 | 228.2 | 81.74 | 59.91* | 43.77* |
| 5.56 | 245.2 | 82.64 | 61.02 | 44.87 |

Figure 3:
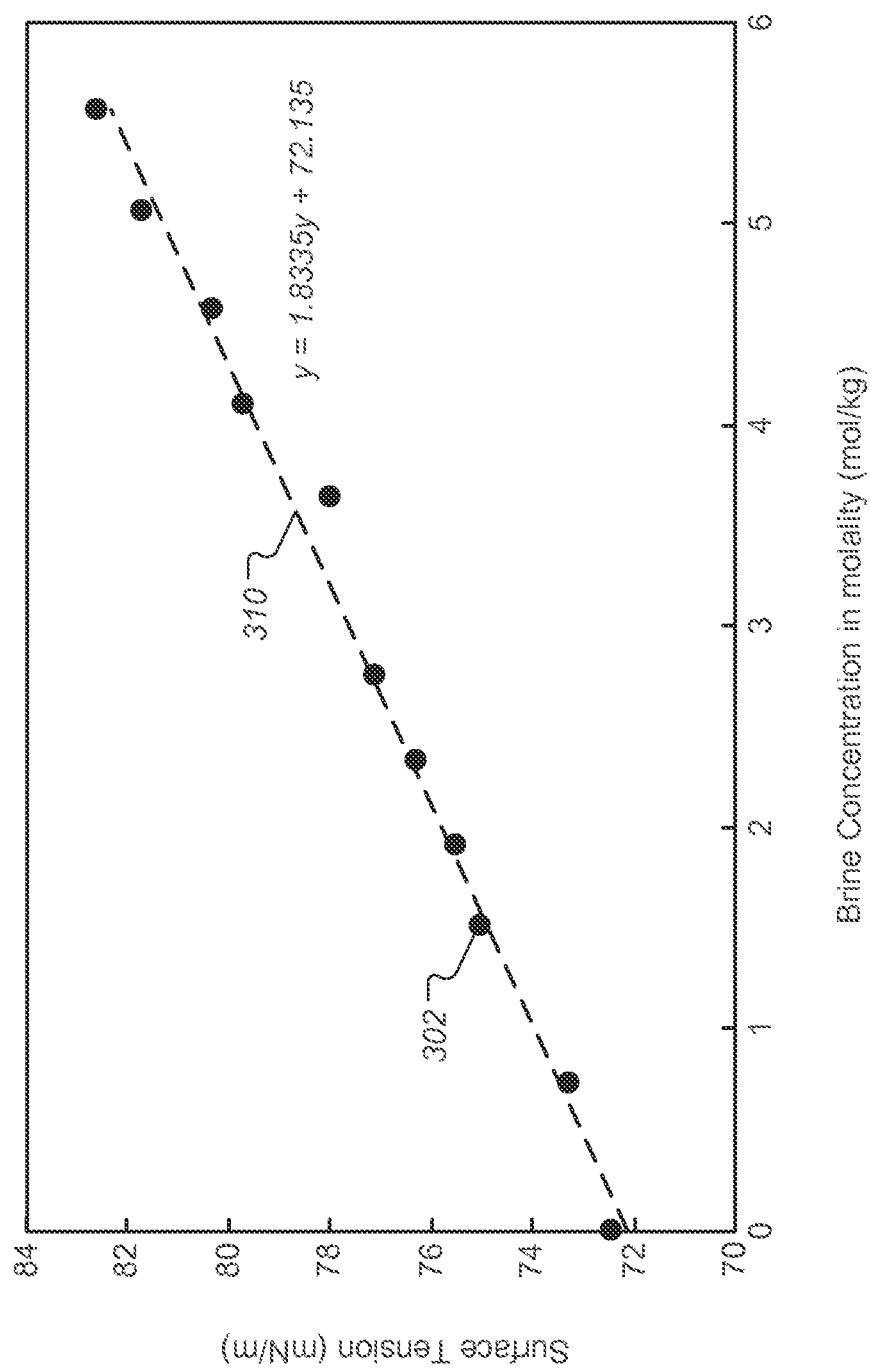
FIG. 3 is a plot showing surface tension of brine as a function of salinity, according to some embodiments.

FIG. 3 is a plot showing surface tension of brine $\gamma_{ba}$ as a function of salinity, according to some embodiments. The black circles such as symbol 302 indicate the experimental data as shown in Table 2 and the dotted line 310 is a fitted linear trend line.

Figure 4:
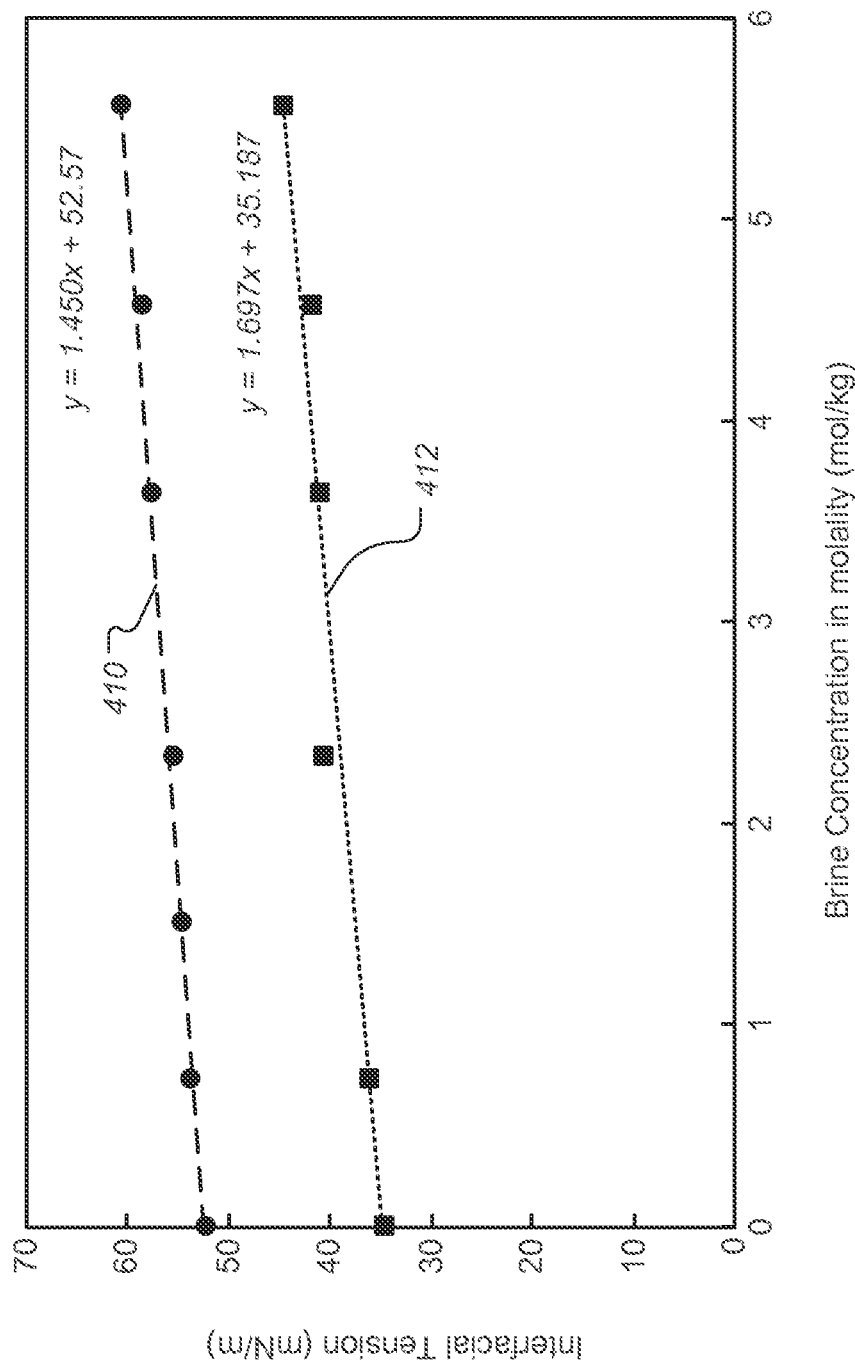
FIG. 4 is a plot showing interfacial tension at brine/oil interface $\gamma_{bo}$ as a function of salinity, according to some embodiments.

FIG. 4 is a plot showing interfacial tension at brine/oil interface $\gamma_{bo}$ as a function of salinity, according to some embodiments. Since $\gamma_{bo}$ exhibits strong time dependence, two sets of values (initial, and after 10 hours relaxation) are provided. The initial data are shown by the circle symbols and trend line 410, while the 10 hour data are shown by the square symbols and trend line 412.

Since the value of brine/oil interfacial tension exhibits strong time dependence, it was decided to consider both initial and long-term equilibrated values and to analyze them in parallel (see Table 2 and FIG. 4). As the result, two $\Delta\gamma_{bo}$ sets can be created (see Table 3). As in the previously described case, the reference state corresponds to the system with DI water (c=0.0). As one can see, $\Delta\gamma_{bo}$ were in all cases negative.

In order to analyze the first term in Eq. 4 an estimate cos $\theta(c_l)$ was used. Since the experimental picture in case of DI water and calcite corresponds to the case shown in FIG. 1-1, we conclude that if we take $c_l$=0.0 as the reference state, then cos $\theta(c_l)$>0 and thus, the total impact of the first term in Eq. 4 in our case is positive. However, the impact in some cases could be negative, depending if $\theta$ is bigger or smaller than $\pi/2$ in the reference state. This should not be a cause of confusion, however. The sign of the first term simply indicates that the change in $\gamma_{bo}$ is an increase ("+") or a decrease ("−") in the spreading of the drop.

What is useful is the relative impact of the IFT and "surface alteration" terms. To estimate it, we can calculate the following ratio:

$$K = \frac{k_{surf\text{-}alt}}{k_{IFT}} = \frac{\frac{1}{\gamma_{boj}(c_h)}\Delta\gamma_{bs}}{\frac{\cos\theta(c_l)}{\gamma_{bo}(c_h)}\Delta\gamma_{bo}} = \frac{\Delta\gamma_{bs}}{\cos\theta(c_l)\Delta\gamma_{bo}} \quad (8)$$

Eq. 8 can factorize into the following two multipliers:

$$\frac{1}{\cos\theta(c_l)}$$

and $$\frac{\Delta\gamma_{bs}}{\Delta\gamma_{bo}}.$$

An estimate can be made for each of the two multipliers separately. The ratio $\Delta\gamma_{bs}/\Delta\gamma_{bo}$ can be calculated based on the data from Tables 1 and 3. For calcite, it varies in the range from 3 to 5 (see Table 4). The value of cos $\theta(c_l)$ can be assumed to be lower than 1. Data provided in Yousef, A. A., Al-Saleh, S., Al-Jawfi, M. 2011, "New recovery method for carbonate reservoirs through tuning the injection water salinity: smart water flooding", SPE 143550, suggest that $\theta(c_1)\approx 70°$ and therefore, cos $\theta(c_l)\approx 0.35$. Thus, K is in the range between 10 and 15. This means that at least 90% change in the contact angle is due to the change in surface/brine interaction, which we refer to herein as "surface alteration" impact.

TABLE 3

| c, (mol/kg) | c, kppm | $\Delta_0\gamma_{bo}$, mN/m | $\Delta_{10h}\gamma_{bo}$, mN/m |
|---|---|---|---|
| 0.00 | 0.00 | 0.00 | 0.00 |
| 1.91 | 100.4 | −2.78 | −3.24 |
| 2.75 | 138.5 | −4.00 | −4.67 |
| 3.64 | 175.4 | −5.30 | −6.18 |

In Table 3, the difference in brine/oil surface tension $\Delta\gamma_{bo}$ for different concentrations of the brine is shown. As the reference state system with DI water (c=0.0) is chosen.

TABLE 4

| Ratio $\Delta\gamma_{bs}/\Delta\gamma_{bo}$ for different brine concentrations. | | | |
|---|---|---|---|
| c, (mol/kg) | c, kppm | $\Delta_3\gamma_{bs}/\Delta_0\gamma_{bo}$, mN/m | $\Delta_{1hr}\gamma_{bs}/\Delta_{10hrs}\gamma_{bo}$, mN/m |
| 0.00 | 0.00 | — | — |
| 1.91 | 100.4 | 3.43 | 5.06 |
| 2.75 | 138.5 | 5.03 | 4.06 |
| 3.64 | 175.4 | 4.85 | 4.61 |

Approach to Contact Angle Measurements.

Apart from the understanding of the relative impact of IFT and "surface alteration" contribution, a new approach to the contact angle measurements will now be described in light of Eq. 4, according to some embodiments.

Figures 1, 5:
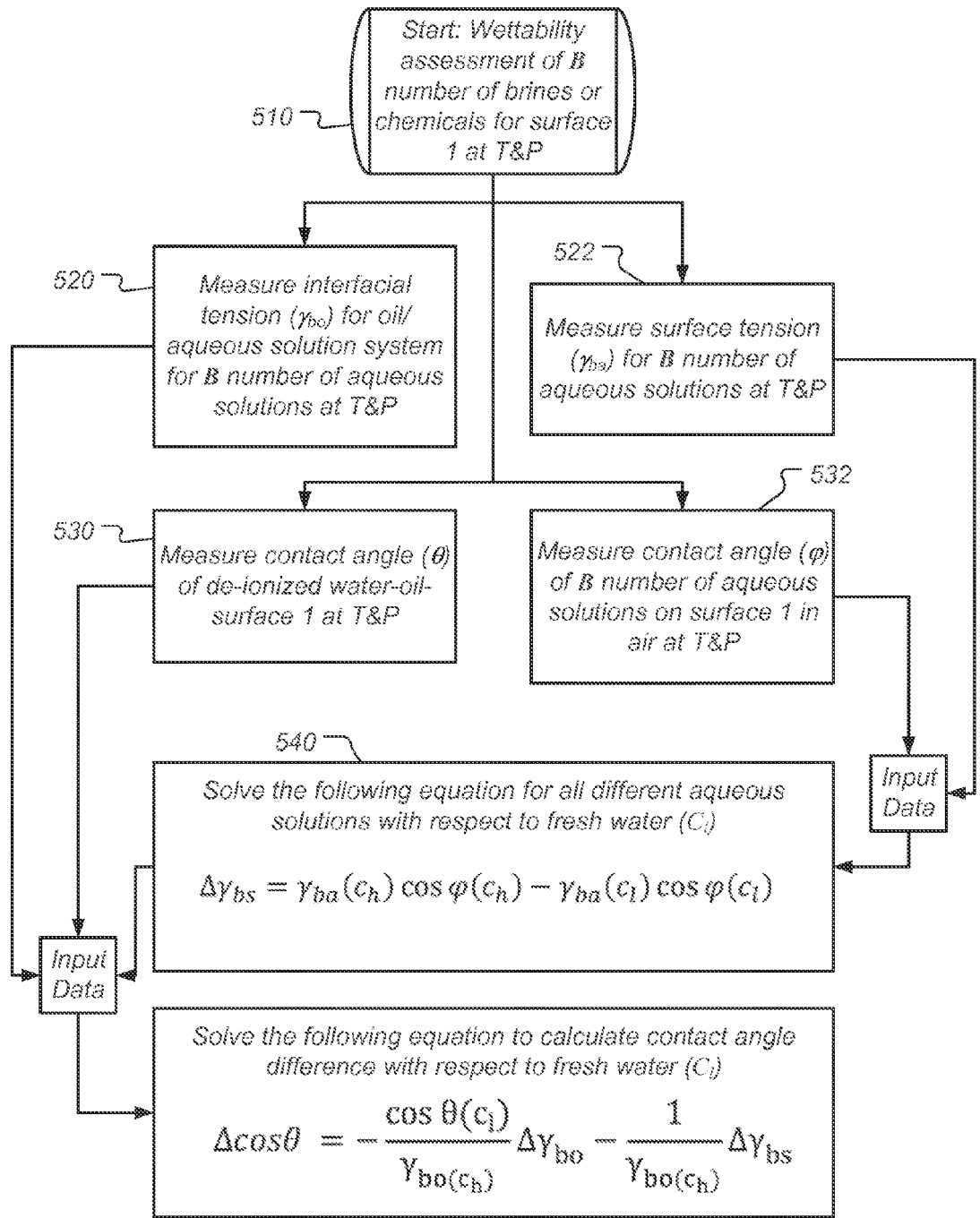
Figures 2, 5:
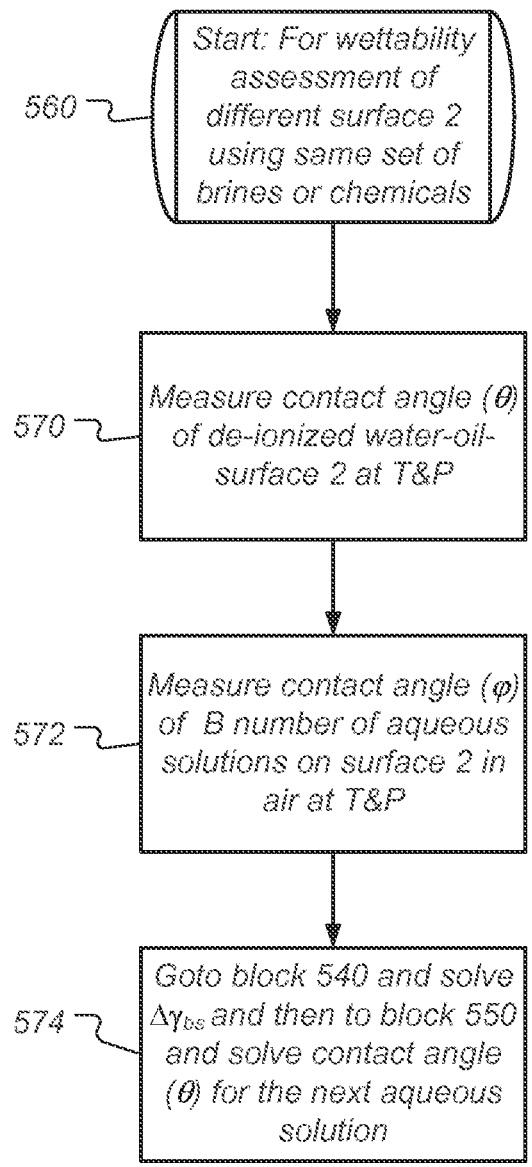

FIGS. 5-1 and 5-2 are flow charts illustrating a protocol for determining contact angle changes, according to some embodiments. The assumed task is to measure contact angle in surface/brine/oil system for different brine salinities and different surfaces. In the case of S different surfaces and B different brine concentrations using a conventional "brute force" approach one would perform S×B measurements in a sealed cell, which is relatively complicated, sensitive and time-consuming. However, a much more elegant path is described, according to some embodiments, in view of a careful analysis of Eq. 4.

Referring to FIG. 5-1, in block 510, the protocol is started in which a wettability assessment is being made of B number of brines or chemicals for a first surface ("surface 1"), at a given temperature and pressure condition ("T&P"). In block 522, surface tension ($\gamma_{ba}$) is measured for B number of aqueous solutions at the given temperature and pressure. In block 532, contact angle ($\varphi$) of B number of aqueous solutions are measured on surface 1 in air at the given temperature and pressure. In block 540, Eq. 5 is solved for all B of the aqueous solutions with respect to fresh water ($c_l$) using the results of blocks 522 and 532.

In block 520, interfacial tension ($\gamma_{bo}$) is measured for oil/aqueous solution system for B number of aqueous solutions at the given temperature and pressure. In block 530, contact angle ($\theta$) of de-ionized water-oil-surface is measured for surface 1 at the given temperature and pressure. In block 550, Eq. 4 is solved using the results of blocks 520, 530 and 540 to calculate the contact angle difference for each of the B solutions with respect to fresh water.

Referring now to FIG. 5-2, in block 560 the protocol continues for wettability assessment of a second surface ("surface 2") using the same set of B brines or chemicals used in the protocol of FIG. 5-1. In block 570, contact angle (θ) of de-ionized water-oil-surface is measured for surface 2 at the given temperature and pressure. In block 572, contact angle (ϕ) of B number of aqueous solutions on surface 2 is measured in air at the given temperature and pressure. In block 574, Eq. 4 and Eq. 5 are again solved to calculate the contact angle difference with respect to fresh water for each of the B fluids on surface 2. In the case of additional surfaces, the protocol of FIG. 5-2 is repeated for each additional surface.

Note that in the described protocol of FIGS. 5-1 and 5-2, we will perform only S measurements in a sealed cell, one experiment for each surface in case of one reference brine (DI water) to have cos $\theta(c_i)$ value for each surface. Then using a much simpler and more precise pendant drop set-up, we perform B measurements in brine/oil system to obtain $\Delta\gamma_{bo}$ for each brine concentration. Knowing these parameters, we can calculate the first term in Eq. 4 for all S×B cases. To be able to calculate the second term in Eq. 4, we calculate $\Delta\gamma_{bs}$ using Eq. 5. To do this, we perform B measurements for pendant drop in air to obtain $\gamma_{ba}$ values and then, we perform S×B measurements of drop of brine at the surface in air to measure values of ϕ. As the result, we make S+2B+S×B measurements, but out of them only S measurements have to be performed in the relatively complex surface/brine/oil environment. Here, we should also take into account that IFT (and thus contact angle θ) in brine/oil systems usually exhibit strong time dependence. This, in turn, results in relatively long relaxation to obtain equilibrium values. Thus, the ability to substitute significant number of brine/oil measurements by measurements in brine/air system saves a significant amount of time while potentially increasing the accuracy of the results.

Comparison with the Experiment.

To demonstrate the applicability of the contact angle measurement method described with respect to FIGS. 5-1 and 5-2, we performed a set of experiments. As a test system, we have chosen a sodium chloride brine/dodecane system with laboratory glass plate as the surface. The system is relatively simple to handle and the homogeneity of the glass can help in repeatability of the results. The sodium chloride brines of concentration c=0 (deionized water), 1.91, 2.75, 3.64, and 5.56 molality (mol/kg) were considered.

The glass/brine/air contact angle ϕ, SFT $\gamma_{ba}$ and IFT $\gamma_{bo}$ values for the considered systems are provided in Table 5. The interfacial tension ($\gamma_{bo}$) values were obtained at the initial moment after the drop creation, $\gamma_{bo}^0$, after 30 minutes, $\gamma_{bo}^{30}$, and after one hour, $\gamma_{bo}^{60}$. The $\gamma_{bo}$ measurements were done in a separate set of experiments, thus, the values may differ from those in Table 2. The results of glass/brine/air contact angle ϕ measurements are under risk to be affected by evaporation of the drop. To avoid evaporation effects, we tried to perform contact angle measurements as fast as possible and in a sealed chamber, which means that the values of ϕ in Table 5 are $\phi|_{t=0}$.

To apply the method of indirect surface/brine/oil contact angle measurements as a function of salinity, one needs to have a reference value of θ, which we imposed to be θ(0) i.e. contact angle for DI water. To obtain a reliable reference value, we performed a number of measurements using three different glass plates. We also tried to look at the contact angle as a function of time. We measured "initial" contact angle value, the contact angle value after 30 minutes and also after "topping" the drop with additional liquid+30 min relaxation. The averaged value for the DI glass/water/dodecane contact angle is $\theta|_{c=0}$=29.8±6.4.

Now using Eq. 5, we can calculate $\Delta\gamma_{bs}$ values; the first and the second terms of Eq. 4 for the three different $\gamma_{bo}$ (see Table 5). Knowing these parameters, it is now possible to calculate the values of contact angle in glass/brine/dodecane for brines of different salinity. To test the calculated values, we performed experimental measurements of the glass/brine/dodecane contact angle for the brines mentioned above. The data are summarized in Table 6. As one can see, the calculated values match the experimentally measured ones within the error bars.

TABLE 5

| c, (mol/kg) | 0 | 1.91 | 2.75 | 3.64 | 5.56 |
|---|---|---|---|---|---|
| <ϕ>, deg | 15.80 | 27.00 | 32.80 | 40.20 | 48.70 |
| $\gamma_{ba}$, mN/m | 72.49 | 75.56 | 77.15 | 78.04 | 82.64 |
| $\gamma^0_{bo}$, mN/m | 52.06 | 55.01 | 56.28 | 57.81 | 61.02 |
| $\Delta\gamma^0_{bo}$, mN/m | 0.00 | -2.95 | -4.22 | -5.75 | -8.96 |
| $\gamma^{30}_{bo}$, mN/m | 40.78 | 47.40 | 43.53 | 51.66 | 54.18 |
| $\Delta\gamma^{30}_{bo}$, mN/m | 0.00 | -6.62 | -2.75 | -10.88 | -13.40 |
| $\Delta\gamma^{60}_{bo}$, mN/m | 40.82 | 46.43 | 42.42 | 49.79 | 52.59 |
| $\Delta\gamma^{60}_{bo}$, mN/m | 0.00 | -5.61 | -1.60 | -8.97 | -11.77 |
| $-\cos\theta(0)\Delta\gamma_{bo}/\gamma_{bo}^0$ | 0.000 | 0.047 | 0.065 | 0.086 | 0.127 |
| $-\cos\theta(0)\Delta\gamma_{bo}/\gamma_{bo}^{30}$ | 0.000 | 0.121 | 0.055 | 0.183 | 0.215 |
| $-\cos\theta(0)\Delta\gamma_{bo}/\gamma_{bo}^{30}$ | 0.000 | 0.105 | 0.033 | 0.156 | 0.194 |
| $\Delta\gamma_{bs}$, mN/m | 0.000 | -2.430 | -4.900 | -10.140 | -15.210 |
| $\Delta\gamma_{bs}/\gamma^0_{bo}$ | 0.000 | -0.044 | -0.087 | -0.175 | -0.249 |
| $\Delta\gamma_{bs}/\gamma^{30}_{bo}$ | 0.000 | -0.051 | -0.113 | -0.196 | -0.281 |
| $\Delta\gamma_{bs}/\gamma^{60}_{bo}$ | 0.000 | -0.052 | -0.116 | -0.204 | -0.289 |

Table 5 shows measured values of contact angle (ϕ), SFT ($\gamma_{ba}$) and IFT ($\gamma_{bo}$) at different brine concentrations.

TABLE 6

| c, (mol/kg) | 0 | 1.91 | 2.75 | 3.64 | 5.56 |
|---|---|---|---|---|---|
| $\theta^{exp}$ | 29.8 ± 6.4 | 38.1 ± 1.9 | 45.1 ± 1.7 | 50.9 ± 3.6 | 58.0 ± 7.0 |
| $\theta^{calc}$ |  | 39.00 | 44.30 | 52.70 | 60.60 |

Table 6 shows contact angle (θ) for a drop at the glass surface as a function of brine concentration, calculated using Eq. 4 with θ(0) as the reference value, $\theta^{calc}$ and measured in the experiment, $\theta^{exp}$.

The experimental contact angle values provided in Table 6 were obtained using the "brine drop created in oil" approach. This approach allows rapid measurements of the contact angle, thus in the calculations we used the "initial" $\gamma_{bo}$ values.

The theoretical model described herein demonstrates that for carbonates 85-90% of the effect related to salinity increase comes from surface alteration, and only 10-15% from change in interfacial tension. The described model is relatively simple and can be utilized in other comparison studies where the source of the dominant impact is not very clear. The accurate determination of both parameters and their ratio is important when it comes to evaluating a potential EOR scenario.

According to some embodiments, the model is used in the described protocol for contact angle measurements of reservoir rocks at different salinity without actually doing the measurements in rock/brine/oil system as would be performed in a conventional "brute force" method. With single contact angle measurement in rock/brine/oil system using fresh water and with other less complicated brine/oil and surface/brine/air laboratory measurements, it is possible to predict the contact angle in the original rock/brine/oil system at different brine concentrations. Our experimental results using a glass/brine/dodecane system with four different brines obtained using a conventional approach agree well with the contact angles predicted using the proposed protocol. According to some embodiments, this approach makes wettability assessment of reservoir rocks less complicated and less sensitive to surface preparation.

Figure 6:
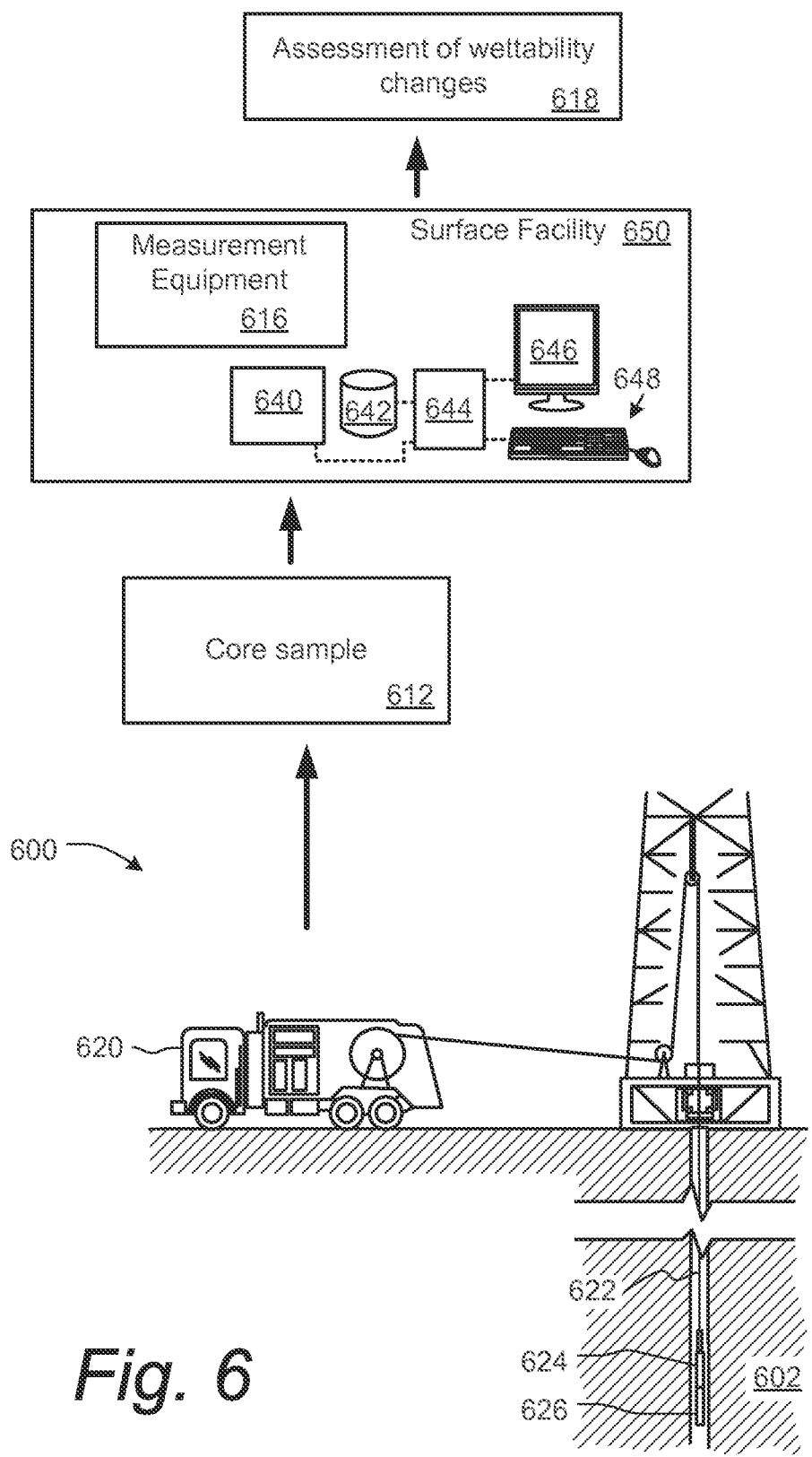
FIG. 6 is a diagram showing aspects of a system for assessing wettability alteration due to fluid changes, according to some embodiments.

FIG. 6 is a diagram showing aspects of a system for assessing wettability alteration due to fluid changes, according to some embodiments. Core samples are being gathered from a subterranean rock formation 602 at wellsite 600 via a wireline truck 620 deploying a wireline tool string in well 626 via wireline 622. The tool string 626 includes one or more wireline tools including a core sampling tool 624. The acquired core sample 612 is transported from the wellsite 600 to a surface facility 650, which includes one or more central processing units 644 for carrying out the data processing procedures as described herein, as well as other processing. Facility also includes a data storage system 642, communications and input/output modules 640, a user display 646 and a user input system 648. According to some embodiments, the surface facility 650 may be located in a location remote from the wellsite 600. Surface facility 650 also includes measurement equipment 616 which is adapted and configured to carry out the measurement procedures such as described in blocks 520, 522, 530, 532, 570 and 572 shown in FIGS. 5-1 and 5-2. The processing units 644 are programmed to carry out the calculations described in blocks 540, 550 and 574 shown in FIGS. 5-1 and 5-2 so as to yield an assessment of wettability changes 618 shown in FIG. 6.

According to some embodiments, the protocols described and shown with respect to FIGS. 5-1 and 5-2 are applied to non-oilfield applications. In general, the techniques described are applicable to the assessment of any wettability alteration due to fluid changes. For example, the contact angle difference between a drop of liquid and a solid surface resulting from a change in the surrounding fluid can be calculated in cases where the drop of liquid is not oil and also where the surrounding fluid is not aqueous. Furthermore, the described technique is also applicable when one or both of the surrounding fluids are gases. In another example variation, the measurements using air in blocks 522, 532 and 572 need not be plain air, but can be another reference gas, such as nitrogen, and according to some embodiments can be any suitable reference fluid. Similarly, according to some embodiments, another reference fluid is used instead of deionized water as a reference fluid in blocks 530 and 570. Wettability alteration assessment techniques, including contact angle changes calculations as described herein, can be applied to other applications where surface wettability plays an important role. Such other applications include, for example: body implants, contact lenses, biomaterials, offset printing processes, packaging, semiconductor wafers, electronic products, biofilm growth, fabrics, superhydrophobic surfaces, self-cleaning and non-sticky surfaces.

Although only a few example embodiments have been described in detail above, those skilled in the art will readily appreciate that many modifications are possible in the example embodiments without materially departing from the subject disclosure. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words 'means for' together with an associated function.

What is claimed is:

1. A method for determining wettability alteration due to fluid changes, the method comprising:
   measuring interfacial tension between a first liquid and a second fluid;
   measuring interfacial tension between the first liquid and a third fluid;
   measuring surface tension between the second fluid and a first reference fluid;
   measuring surface tension between the third fluid and the first reference fluid;
   measuring contact angle of the first liquid and a first solid surface in a second reference fluid;
   measuring contact angle of the second fluid and the first solid surface in the first reference fluid;
   measuring contact angle of the third fluid and the first solid surface in the first reference fluid; and
   determining a change in wettability for the first solid surface and the first liquid due to a change from the second fluid to the third fluid based at least in part on the measurements of interfacial tensions, surface tensions and contact angles.

2. A method according to claim 1, wherein said measurements are carried out using the same temperature and pressure.

3. A method according to claim 1, wherein the first reference fluid is air.

4. A method according to claim 1, wherein the second reference fluid is deionized water.

5. A method according to claim 1, wherein the second fluid is a liquid and the third fluid is a gas.

6. A method according to claim 1, wherein the second and third fluids are liquids.

7. A method according to claim 1, further comprising:
   measuring contact angle of the first liquid and a second solid surface in the second reference fluid;
   measuring contact angle of the second fluid and the second solid surface in the second reference fluid;
   measuring contact angle of the third fluid and the second solid surface in the second reference fluid; and
   determining change in wettability for the second solid surface and the first liquid due to a change from the second fluid to the third fluid based at least in part on the measurements of interfacial tensions, surface tensions, and contact angles with the second solid surface.

8. A method according to claim 7, wherein said steps involving the second solid surface are repeated for a third solid surface.

9. A method according to claim 1, further comprising:
measuring interfacial tension between the first liquid and a fourth fluid;
measuring surface tension between the fourth fluid and the first reference fluid; and
measuring contact angle of the fourth fluid and the first solid surface in the second reference fluid, wherein said determining a change in wettability is further due to a change including the fourth fluid.

10. A method according to claim 1, wherein said determining a change in wettability includes calculating a change in contact angle between the first liquid and the first solid surface due to a change from the second fluid to the third fluid.

11. A method according to claim 10, wherein said calculating a change in contact angle is based on a relationship between change in contact angle and an interfacial tension term and a surface alteration term, the interfacial tension term relating to a change in interfacial tension from between the first liquid and the second fluid to between the first liquid and the third fluid, and the surface alteration term relating to a change in interfacial tension from between the second fluid and the first surface to between the third fluid and the first surface.

12. A method according to claim 11, wherein the relationship is equivalent to $$\Delta \cos\theta = -\frac{\cos\theta(c_l)}{\gamma_{bo}(c_h)}\Delta\gamma_{bo} - \frac{1}{\gamma_{bo}(c_h)}\Delta\gamma_{bs}$$

where $c_l$ represents the second fluid, $c_h$ represents the third fluid, $\eta$ is the contact angle between the first liquid and the first solid surface, $\gamma_{bo}$ is interfacial tension between the first liquid and the second and third fluids; and $\gamma_{bs}$ is surface tension between the first surface and the second and third fluids.

13. A method according the claim 12, wherein the surface alteration term is calculated using a relationship equivalent to $$\Delta\gamma_{bs} = \gamma_{ba}(c_h)\cos\phi(c_h) - \gamma_{ba}(c_l)\cos\phi(c_l)$$

where $\phi$ represents contact angles between the second and third fluids and the first surface.

14. A method according to claim 1, wherein the first surface is a surface on a sample of rock from a subterranean hydrocarbon-bearing reservoir rock formation, the first liquid is an oil, and the second and third fluids are aqueous liquids.

15. A method according claim 14, wherein the second and third fluids are brines having different compositions.

16. A method according to claims 14, wherein the sample of rock is a core sample taken from the subterranean rock formation.

17. A method according to claim 14, wherein said steps of measuring are carried out using a temperature and pressure found in the subterranean rock formation.

18. A system for determining wettability alteration due to fluid changes, the system comprising a computer configured and programmed to receive data representing measurements of (1) interfacial tension between a first liquid and a second fluid, (2) interfacial tension between the first liquid and a third fluid, (3) surface tension between the second fluid and a first reference fluid, (4) surface tension between the third fluid and the first reference fluid, (5) contact angle of the first liquid and a first solid surface in a second reference fluid, (6) contact angle of the second fluid and the first solid surface in the second reference fluid, and (7) contact angle of the third fluid and the first solid surface in the first reference fluid, and to determine a change in wettability for the first solid surface and the first liquid due to a change from the second fluid to the third fluid, the determination being based at least in part on the data representing the measurements of interfacial tensions, surface tensions and contact angles.

19. A system according to claim 18, wherein the first reference fluid is air, the second reference fluid is deionized water and the second and third fluids are liquids.

20. A system according to claim 18, further comprising measurement equipment configured to make the measurements of interfacial tension, surface tension and contact angle.

21. A system according to claim 20, wherein the measurement equipment is configured to carry out the measurements of interfacial tension, surface tension and contact angle at a constant temperature and pressure.

22. A system according to claim 18, further comprising a borehole deployable core sampling tool adapted and configured to obtain a core sample from a subterranean hydrocarbon-bearing reservoir rock formation, wherein the first solid surface is a surface on a sample of rock from a core sample taken from the subterranean rock formation.

23. A system according to claim 22, wherein the first liquid is an oil, the second and third fluids are aqueous liquids, and the second and third fluids are brines having different compositions.

24. A system according to claim 18, wherein the change in wettability determination includes calculating a change in contact angle between the first liquid and the first solid surface due to a change from the second fluid to the third fluid.

25. A system according to claim 24, wherein said calculating a change in contact angle is based on a relationship between change in contact angle and an interfacial tension term and a surface alteration term, the interfacial tension term relating to a change in interfacial tension from between the first liquid and the second fluid to between the first liquid and the third fluid, and the surface alteration term relating to a change in interfacial tension from between the second fluid and the first surface to between the third fluid and the first surface.

26. A method for determining wettability alteration of a rock surface by oil due to brine concentration changes, the method comprising:
measuring interfacial tension between an oil and a first brine composition;
measuring interfacial tension between the first oil and a second brine composition;
measuring surface tension between the first brine composition and air;
measuring surface tension between the second brine composition and air;
measuring contact angle of the oil and a first solid surface in fresh water, the first solid surface being a surface from a core sample of a subterranean hydrocarbon-bearing reservoir rock formation;
measuring contact angle of the first brine composition and the first solid surface in fresh water;
measuring contact angle of the second brine composition and the first solid surface in fresh water; and
determining a change in wettability for the first solid surface and the oil due to a change from the first brine composition to the second brine composition based at least in part on the measurements of interfacial tensions, surface tensions and contact angles.

27. A method according to claim 26, wherein the fresh water is deionized water.

28. A method according to claim 26, further comprising:
measuring contact angle of the oil and a second solid surface in fresh water;
measuring contact angle of the first brine composition and the second solid surface in air;
measuring contact angle of the second brine and the second solid surface in air; and
determining change in wettability for the second solid surface and the oil due to a change from the first brine composition to the second brine composition based at least in part on the measurements of interfacial tensions, surface tensions, and contact angles with the second solid surface.

29. A method according to claim 28, wherein the second solid surface is from a second core sample of the subterranean rock formation.

30. A method according to claim 28, wherein the second solid surface is a different location on said core sample than the first solid surface.

* * * * *